(12) United States Patent
Milliman et al.

(10) Patent No.: US 9,820,748 B2
(45) Date of Patent: Nov. 21, 2017

(54) INSERTION AID WITH INTERFERENCE FIT

(75) Inventors: Keith L. Milliman, Bethel, CT (US);
Thomas Wenchell, Durham, CT (US);
Philip C. Roy, Orange, CT (US)

(73) Assignee: Covidien LP, Mansfield, MA (US)

( * ) Notice: Subject to any disclaimer, the term of this patent is extended or adjusted under 35 U.S.C. 154(b) by 1355 days.

(21) Appl. No.: 12/233,824

(22) Filed: Sep. 19, 2008

(65) Prior Publication Data

US 2009/0082777 A1  Mar. 26, 2009

Related U.S. Application Data

(60) Provisional application No. 60/995,025, filed on Sep. 24, 2007, provisional application No. 61/074,756, filed on Jun. 23, 2008.

(51) Int. Cl.
| | | |
|---|---|---|
| A61B 17/04 | (2006.01) | |
| A61B 17/115 | (2006.01) | |
| A61B 17/11 | (2006.01) | |
| A61B 17/00 | (2006.01) | |

(52) U.S. Cl.
CPC ......... *A61B 17/115* (2013.01); *A61B 17/1114* (2013.01); *A61B 2017/00473* (2013.01); *A61B 2017/00477* (2013.01)

(58) Field of Classification Search
CPC . A61B 17/068; A61B 17/0686; A61B 17/115; A61B 17/1155
USPC .............. 227/175.1; 606/86 R, 99, 104, 142, 606/151–153, 219
See application file for complete search history.

(56) References Cited

U.S. PATENT DOCUMENTS

| | | | |
|---|---|---|---|
| 4,505,272 A * | 3/1985 | Utyamyshev et al. .... | 227/179.1 |
| 4,817,847 A | 4/1989 | Redtenbacher et al. | |
| 4,848,367 A | 7/1989 | Avant et al. | |
| 4,873,977 A | 10/1989 | Avant et al. | |
| 5,047,039 A | 9/1991 | Avant et al. | |
| D331,971 S | 12/1992 | Main | |
| 5,197,648 A | 3/1993 | Gingold | |
| 5,275,322 A * | 1/1994 | Brinkerhoff et al. ...... | 227/175.1 |
| 5,314,435 A | 5/1994 | Green et al. | |
| 5,443,198 A * | 8/1995 | Viola ................... | A61B 17/072 227/175.1 |
| 5,464,415 A | 11/1995 | Chen | |
| 5,522,534 A | 6/1996 | Viola et al. | |
| 5,531,785 A | 7/1996 | Love et al. | |
| 5,669,918 A * | 9/1997 | Balazs et al. ................. | 606/139 |
| 5,718,360 A * | 2/1998 | Green et al. ................ | 227/179.1 |
| 5,836,503 A * | 11/1998 | Ehrenfels et al. .......... | 227/175.1 |
| 5,860,581 A * | 1/1999 | Robertson ........... | A61B 17/1114 227/179.1 |
| 6,050,472 A | 4/2000 | Shibata | |

(Continued)

FOREIGN PATENT DOCUMENTS

EP  0803229  10/1997

*Primary Examiner* — Matthew Lawson (57) ABSTRACT

The present disclosure relates to an insertion device including a shaft with a head supported on a distal end thereof. The shaft includes a proximal end with an engagement member that is configured to frictionally engage a distal end of a surgical fastening apparatus such that an interference fit is created therebetween to facilitate selective detachment of the insertion device from the surgical fastening apparatus. The head has an atraumatic configuration, and is dimensioned to be received in a body orifice.

22 Claims, 5 Drawing Sheets

(56) References Cited

U.S. PATENT DOCUMENTS

| | | | |
|---|---|---|---|
| 6,083,241 A | 7/2000 | Longo et al. | |
| 6,102,271 A | 8/2000 | Longo et al. | |
| 6,258,107 B1 | 7/2001 | Balazs et al. | |
| 7,182,239 B1 * | 2/2007 | Myers | A61B 17/115 227/175.1 |
| 7,901,416 B2 * | 3/2011 | Nolan | A61B 17/1114 227/175.1 |
| 7,976,495 B2 | 7/2011 | DeLegge et al. | |
| 8,006,701 B2 * | 8/2011 | Bilotti et al. | 128/898 |
| 2009/0250502 A1 * | 10/2009 | Milliman | 227/179.1 |

* cited by examiner

INSERTION AID WITH INTERFERENCE FIT

CROSS-REFERENCE TO RELATED APPLICATIONS

This application claims the benefit of, and priority to, U.S. Provisional Application Ser. No. 60/995,025, filed on Sep. 24, 2007, and U.S. Provisional Application Ser. No. 61/074,756, filed on Jun. 23, 2008, the entire contents of which are incorporated by reference herein.

BACKGROUND

1. Technical Field

The present disclosure relates generally to surgical instruments and, more particularly, to an insertion device for use with a surgical fastening apparatus.

2. Description of Related Art

During certain surgical procedures, it is often necessary to insert one or more surgical instruments into a body cavity, e.g. through a natural opening, or orifice, or through a percutaneous incision. In surgical procedures involving hollow organ tissue sections, such as colon surgery, it is often necessary to remove a diseased or damaged hollow organ tissue section and insert a surgical apparatus trans-anally in order to reconnect the healthy tissue sections.

In one known method relating to the resection of a target portion of the colon, a fastening apparatus, such as a surgical stapler or multi-part fastening device, is inserted trans-anally. See, e.g., U.S. Pat. No. 5,119,983, the entire contents of which are incorporated by reference herein. During the procedure, the fastening component of the fastening apparatus is positioned within the colon on one side of the target portion that is to be removed. The fastening apparatus is then inserted into the patient's body either through a natural body orifice or through a surgically created opening. The fastening apparatus is positioned within the colon on the other side of the target portion so that the healthy sections surrounding the target portion can be attached together. The fastening component is then connected to the fastening apparatus, and the healthy sections are brought into abutment and fastened together. The fastening apparatus is then removed from the patient.

Various apparatus are suggested in the art that may be used to facilitate the insertion of a fastening apparatus into a body orifice and through a body lumen. For example, it has been suggested that a stapling anvil can be attached to the fastening apparatus in an effort to provide a blunt surface that may be advanced through the body orifice or opening in the patient's tissue. Alternatively, U.S. Pat. No. 5,404,870 discloses a device having a sheath that is open at both ends, through which a fastening apparatus may be inserted into a body orifice. U.S. Pat. No. 5,836,503 discloses an insertion device for use with a surgical fastening apparatus that includes a distal end configured to facilitate the trans-anal insertion of the apparatus and subsequent movement of the apparatus through a body lumen.

Despite the existence of each of the aforedescribed apparatus, it would be advantageous to provide a device that safely and efficiently facilitates the insertion of a surgical fastening apparatus into and/or through a body orifice or opening in a patient's tissue while being readily removable thereafter.

SUMMARY

In one aspect of the present disclosure, an insertion device is disclosed that includes a shaft having a proximal end with an engagement member that is configured to frictionally engage a distal end of a surgical fastening apparatus. The frictional engagement creates an interference fit between the insertion device and the surgical fastening apparatus, which facilitates selective detachment of the insertion device to enable subsequent attachment of an anvil assembly to the surgical fastening apparatus. The insertion device also includes a head supported on a distal end of the shaft. The head has an atraumatic configuration and is dimensioned to be received in a body orifice. The head preferably defines a radius that is at least substantially equal to a radius of a distal end of the surgical fastening apparatus.

In one embodiment of the insertion device, the head may include at least one attachment surface. The at least one attachment surface may be configured as a throughbore formed in the head, or alternatively, may include a cross-member positioned within a recess defined in an external surface of the head. The at least one attachment surface can be configured to engage at least one removal member including a first end and a second end, wherein at least the first end of the at least one removal member is in engagement with the at least one attachment surface. Suitable, illustrative examples of the at least one removal member include a suture, a wire, and a cable.

It is envisioned that the head and the shaft of the insertion device may be integrally formed. Alternatively, however, the shaft and the head may include corresponding structure configured and dimensioned to facilitate selective attachment of the shaft and the head. In such embodiments, the shaft may include at least one protrusion, e.g., a rib, extending radially outward from the distal end of the shaft, and the head may include internal receipt structure, with the at least one protrusion defining a first transverse dimension greater than a second transverse dimension defined by the internal receipt structure such that the shaft frictionally engages the head to establish an interference fit therebetween upon assembly.

To establish frictional engagement between the insertion device and the surgical fastening apparatus, and thus, the aforementioned interference fit therebetween, in one embodiment of the insertion device, the shaft includes an engagement member configured and dimensioned to engage an internal wall at the distal end of the surgical fastening apparatus. The engagement member may include at least one protrusion, e.g., a rib, that extends radially outward from the shaft to engage the internal wall, defining a first transverse dimension that is greater than a second transverse dimension defined by the internal wall.

In another aspect of the present disclosure, a method of performing a surgical procedure is disclosed. The method includes the steps of providing a surgical instrument including a fastening component releasably attachable to a distal end thereof, positioning the fastening component within a patient, providing an insertion device, attaching the insertion device to the distal end of the surgical instrument, advancing the surgical instrument and the insertion device distally through a body orifice, detaching the insertion device from the surgical instrument, attaching the fastening component to the distal end of the surgical instrument, connecting adjacent tissue portions, removing the insertion device, and withdrawing the surgical instrument.

The insertion device of the above method includes a shaft having a proximal end with an engagement member that is configured to frictionally engage a distal end of the surgical instrument such that an interference fit is created therebetween to facilitate selective detachment of the insertion device from the surgical instrument. The insertion device further includes a head supported on a distal end of the shaft. The head has an atraumatic configuration and is dimensioned to be received in a body orifice.

It is also envisioned that insertion device may include a head having at least one attachment surface. In this embodiment, the disclosed method may further include the step of attaching a removal member to the at least one attachment surface formed on the head that is configured and dimensioned for grasping to facilitate removal of the insertion device. In this embodiment, the step of removing the insertion device preferably includes grasping the removal member.

In one embodiment, to detach the insertion device from the surgical instrument, the surgical instrument may be manipulated such that the insertion device is advanced distally relative to a proximal end of the surgical instrument, thereby forcing the insertion device out of frictional engagement with the distal end of the surgical instrument. In one embodiment, the surgical instrument may include a handle assembly positioned at a proximal end and a retaining member at a distal end that is configured and dimensioned for removable positioning within the shaft of the insertion device. In this embodiment, the step of detaching the insertion device from the surgical instrument includes manipulating the handle assembly to thereby advance the retaining member distally, whereby distal advancement of the retaining member effectuates distal advancement of the insertion device.

These and other features of the insertion device, surgical fastening apparatus, and associated methods of performing a surgical procedure described herein will become more readily apparent to those skilled in the art from the following detailed description of various embodiments of the present disclosure.

BRIEF DESCRIPTION OF THE DRAWINGS

The accompanying drawings, which are incorporated in, and constitute a part of this specification, illustrate embodiments of the disclosure and, together with a general description of the disclosure given above and the detailed description of the embodiment(s) given below, serve to explain the principles of the disclosure, wherein.

DETAILED DESCRIPTION OF VARIOUS EMBODIMENTS

Various embodiments of the presently disclosed insertion device will now be described in detail with reference to the foregoing figures wherein like reference numerals identify similar or identical elements. In the figures, and in the description which follows, the term "proximal", as is traditional, will refer to the end of the device that is closer to the clinician, while the term "distal" will refer to the end of the device that is further from the clinician. In addition, the term "fastening apparatus" should be understood to include any device configured to attach one section of tissue to another, including but not being limited to a circular surgical stapler, such as the anastomosis surgical stapling instrument disclosed in U.S. Pat. No. 5,005,749, a multipart surgical fastening device, such as the fragmentable anastomosis ring applier disclosed in U.S. Pat. No. 5,376,098, or a circular anastomosis apparatus, such as the one disclosed in U.S. Pat. No. 5,119,983, the entire contents of which are each incorporated by reference herein. Finally, the terms "body orifice" should be understood to include any opening formed in tissue, either pre-existing or created by a practitioner.

Figure 1:
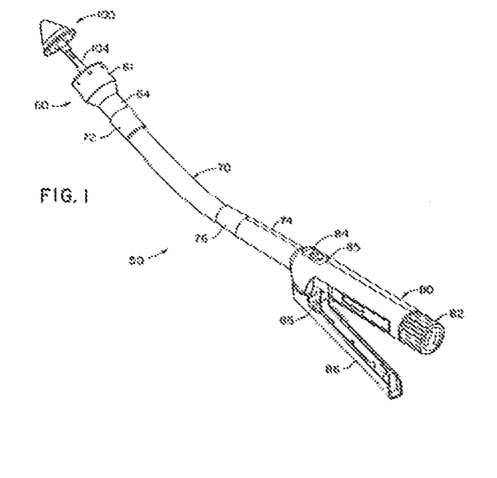
FIG. 1 is a side schematic view of an insertion device in accordance with a first embodiment of the present disclosure including an attachment surface in engagement with a removal member.

FIG. 1 illustrates one embodiment of the presently disclosed insertion device 10 that is the subject of the present disclosure. Insertion device 10 includes a head 12 with a shaft 14 extending proximally therefrom that is configured to releasably engage a fastening apparatus 100 (FIG. 2) so as to facilitate the insertion of the fastening apparatus 100 into a patient's orifice or body cavity.

Figure 2:
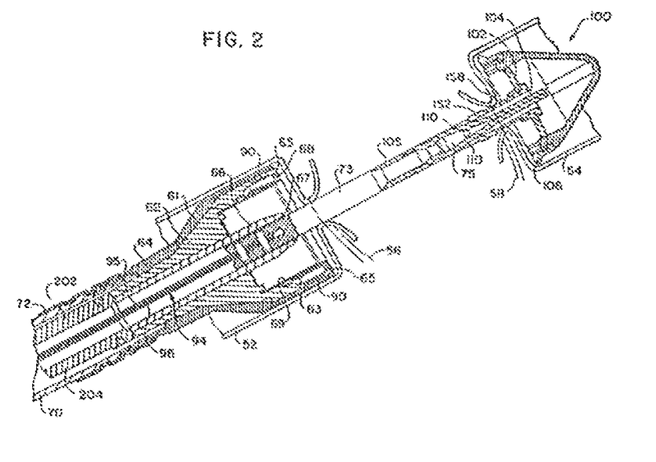
FIG. 2 is a side perspective view of a surgical fastening apparatus for use with the insertion device of FIG. 1.

Turning now to FIG. 2, fastening apparatus 100 will briefly be discussed. Fastening apparatus 100 includes a proximal handle assembly 102, an elongated central body portion 104 and a distal head portion 106. The length, shape and/or the diameter of the central body portion 104 and the head portion 106 may be varied to suit a particular surgical procedure. Head portion 106 includes a retaining member 108 that extends distally beyond a shell assembly 110. Retaining member 108 includes an annular protrusion 112 that is configured to releasably engage a corresponding structure on a fastening component (not shown), e.g. an anvil assembly, as well as on the insertion device 10 (FIG. 1) that is the subject of the present disclosure, as discussed in further detail below. Further details regarding fastening apparatus 100 may be obtained through reference to U.S. Pat. No. 7,168,604, the entire contents of which are incorporated by reference herein.

Although the insertion device 10, and the various embodiments thereof, are described and depicted in connection with the fastening apparatus 100 of FIG. 2, it should be understood that the insertion device 10 may be used with any number of surgical devices where it is desirable to facilitate the insertion thereof into a patient's orifice or body cavity.

Referring again to FIG. 1, head 12 of insertion device 10 includes a smooth, atraumatic leading or outer surface 16 defining a radius that is at least substantially equal to the maximum radius of the distal end of the fastening apparatus 100 (FIG. 2) to which the insertion device 10 is to be attached. The size and configuration of head 12 facilitates insertion of fastening apparatus 100 into a body orifice and substantially prevents tissue from entering the shell assembly 110 of the fastening apparatus 100 during insertion. Head 12 has a proximal end 18 that is connected to the shaft 14, and a substantially rounded distal end 20. To facilitate the releasable attachment of shaft 14 to the retaining member 108 (FIG. 2) of the fastening apparatus 100 to the insertion device 10, the shaft 14 of the insertion device 10 includes a plurality of flexible fingers 22 and an internal shoulder 24 that is configured to releasably engage a corresponding annular protrusion 112 (FIG. 2) formed on the retaining member 108, as discussed in further detail below. The head 12 and the shaft 14 may be formed of any suitable biocompatible material, including but not being limited to stainless steel or polymeric materials, and may be formed by various methods, e.g. injection molding.

Head 12 includes an attachment surface 26 configured to engage a removal member 28. In the figures and description hereinbelow, each embodiment of the present disclosure will be discussed, and depicted in the corresponding figures, as including a single attachment surface 26 and a single removal member 28. However, the incorporation of one or more additional attachment surfaces 26 and removal members 28 is also within the scope of the present disclosure.

In one embodiment, as seen in FIG. 1, the attachment surface 26 is configured as a throughbore 30 formed in the head 12 of device 10. In this embodiment, the attachment surface 26 is configured to receive the removal member 28 such that the removal member 28 passes through the head 12 of device 10. The removal member can be in the form of a suture, wire or other flexible member insertable through the bore to enable removal.

Figure 3:
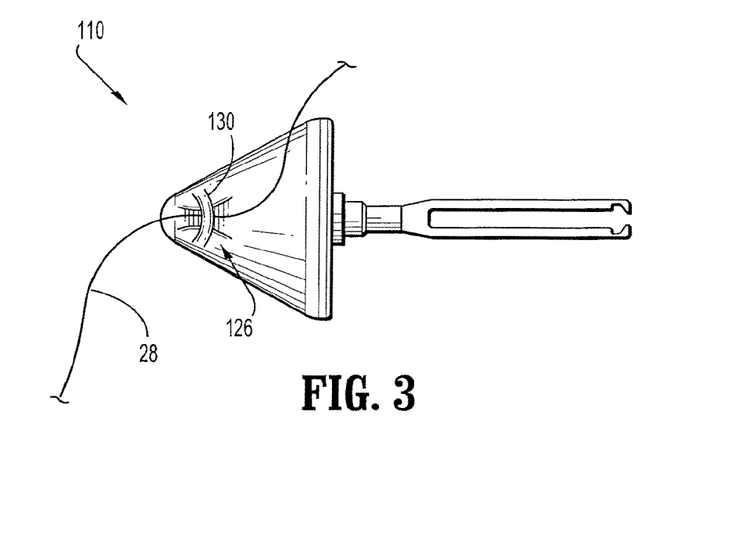
FIG. 3 is a side schematic view of an alternate embodiment of the insertion device of the present disclosure.

As seen in FIG. 3, in an alternate embodiment, an insertion device 110 is disclosed that includes an attachment surface 126 configured as a partial recess or depression formed in head 112 such that a cross-member 130 is defined. In this embodiment, removal member 28 is passed beneath the cross-member 130 and is thereafter attached to the cross-member 130 in any suitable manner, e.g. the removal member 28 is tied around the cross-member 130. It is noted that cross-member 130 preferably defines a smooth continuous surface along the exterior of head 112 to prevent snagging or tearing of tissue. The removal member in this embodiment as well as the other embodiments described herein can be in the form of a suture, wire or other flexible member.

Referring now to FIGS. 1 and 2, following the detachment of device 10 from fastening apparatus 100, the clinician may remove device 10 from the patient by grabbing or grasping removal member 28, or any other portion of device 10 if more easily accessible. The present disclosure contemplates the grasping of removal member 28, or the device 10, itself, through any suitable means, including but not being limited to using a grasping apparatus (not shown) or the clinician's hand.

Figure 4:
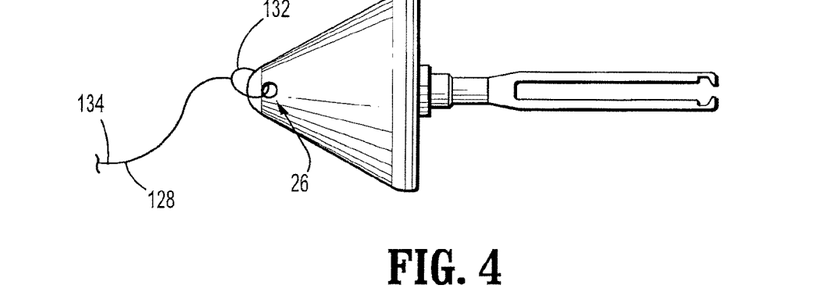
FIG. 4 is a side schematic view of another alternate embodiment of the insertion device wherein the removal member has a first end attached to the attachment surface.
Figure 5:
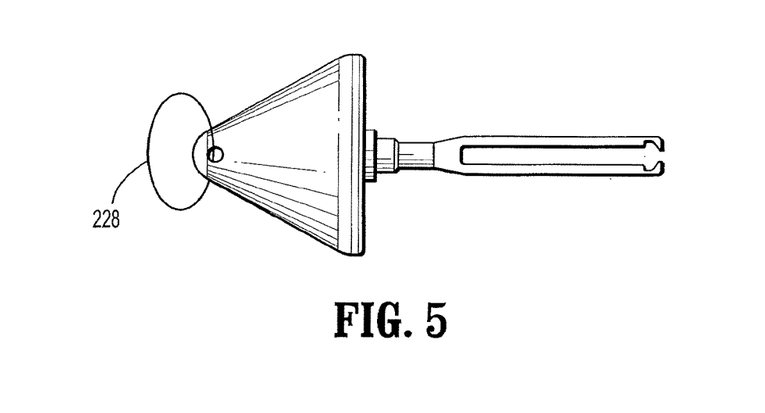
FIG. 5 is a side schematic view of an alternate embodiment having a removal member having a substantially annular configuration in engagement with the insertion device of FIG. 1.

The removal member 28 may be associated with the attachment surface 26 in any manner that facilitates the grasping thereof. As seen in FIG. 4, in one embodiment, a removal member 128 is disclosed that includes a first end 132 that is connected to attachment surface 26 while a second end 134 thereof remains free. Alternately, each of the respective first and second ends 132, 134 of removal member 128 may be connected to the attachment surface 26, either releasably or fixedly, as discussed above. As seen in FIG. 5, in an alternate embodiment, a removal member 228 is disclosed that exhibits a substantially annular configuration, e.g. a substantially elliptical or circular configuration, that is devoid of the respective first and second ends 132, 134 of the removal member 128 (FIG. 4).

Figure 6:
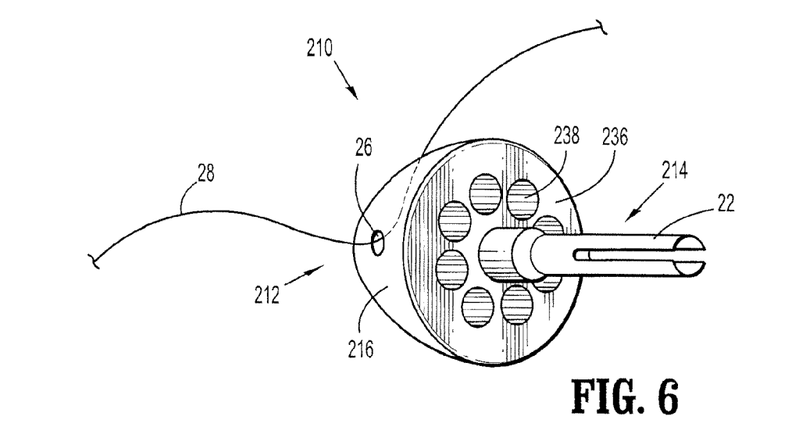
FIG. 6 is another embodiment of the insertion device of FIG. 1 incorporating a plurality of bores.
Figure 7:
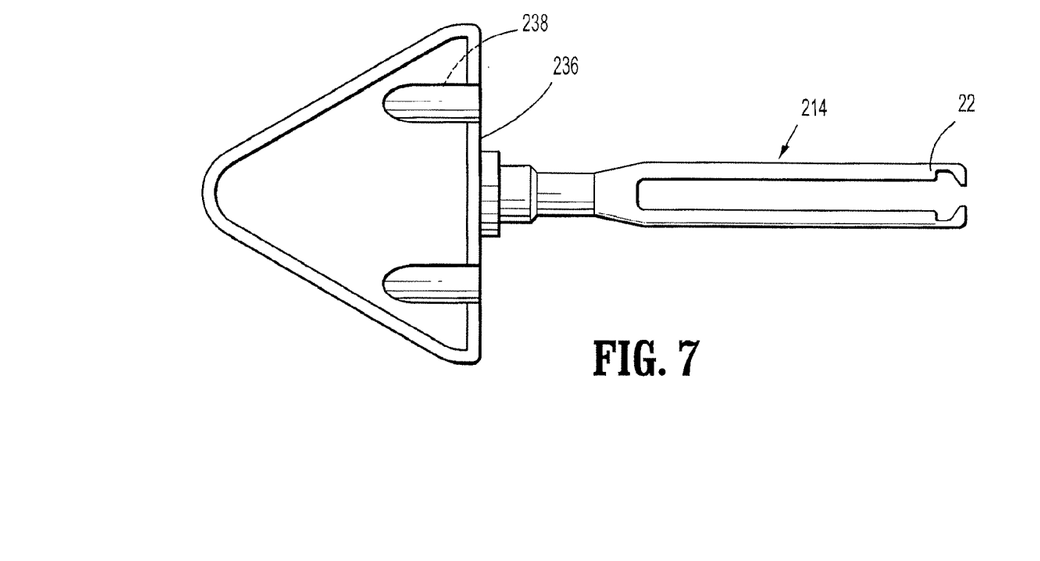
FIG. 7 is a side view of the insertion device of FIG. 6.

FIGS. 6 and 7 depict another embodiment of the insertion device that is the subject of the present disclosure. Insertion device 210 performs substantially in accordance with the insertion device 10 (FIG. 1) discussed above and generally includes a head 212 with a smooth, atraumatic leading outer surface 216, and a shaft 214 that extends proximally therefrom. In this embodiment, head 212 has a substantially flat proximal surface 236 that is oriented so as to be substantially perpendicular to a longitudinal axis of the shaft 214. Proximal surface 236 includes a plurality of recesses or bores 238 that serve to reduce the weight of insertion device 210 as well as reduce any suction effects that may be created between tissue and a surgical fastening device (not shown). In addition, head 212 includes at least one attachment surface 26 (or alternatively 126 of FIG. 3) that is configured to engage at least one removal member 28, as discussed above with respect to each of the embodiments of FIGS. 1 and 3-5. Similar to that of insertion device 10 discussed above, shaft 214 of insertion device 210 includes flexible fingers 22 and an internal shoulder (not shown) such that the insertion device 210 is configured for releasable engagement with the distal end of a fastening apparatus 100 (FIG. 2).

Referring again to FIG. 1, the shaft 14 of the insertion device 10 will be discussed. Shaft 14 generally includes a shaft barrel 32 that defines a lumen 34 extending at least partially therethrough and flexible fingers 22. The lumen 34 includes the internal shoulder 24 configured to releasably engage the annular protrusion 112 (FIG. 2) formed on the retaining member 108 of the fastening apparatus 100.

Upon insertion of the retaining member 108 (FIG. 2) into the lumen 34, the flexible fingers 22 are splayed radially outward such that the retaining member may be received. As the retaining member 108 is advanced distally through the lumen 34, the annular protrusion 112 engages the internal shoulder 24, thereby releasably securing the insertion device 10 to the fastening apparatus. Further details regarding the releasable engagement of the insertion device 10 with the retaining member 108 of the surgical fastening apparatus 100 may be obtained through reference to U.S. Pat. No. 7,168,604.

In alternate embodiments of insertion device 10, the annular protrusion 112 (FIG. 2) and the corresponding receiving structure 22 of the shaft 14 of the insertion device 10 may be any structure suitable for the intended purpose of facilitating the releasable engagement and disengagement of the insertion device 10 and the surgical fastening apparatus 100.

In one embodiment of the insertion device 10, the shaft barrel 32 is releasably connected to the head 12. In this embodiment, the shaft barrel 32 may be connected to the head 12 in any suitable manner, including but not being limited to a threaded connection or snap-fit arrangement therebetween, such that the head 12 is interchangeable with a variety of shafts, thereby facilitating the use of device 10 with a variety of fastening apparatus 100 (FIG. 2). In an alternate embodiment of the device 10, the shaft barrel 32 and the head 12 may be integrally formed.

Figure 8:
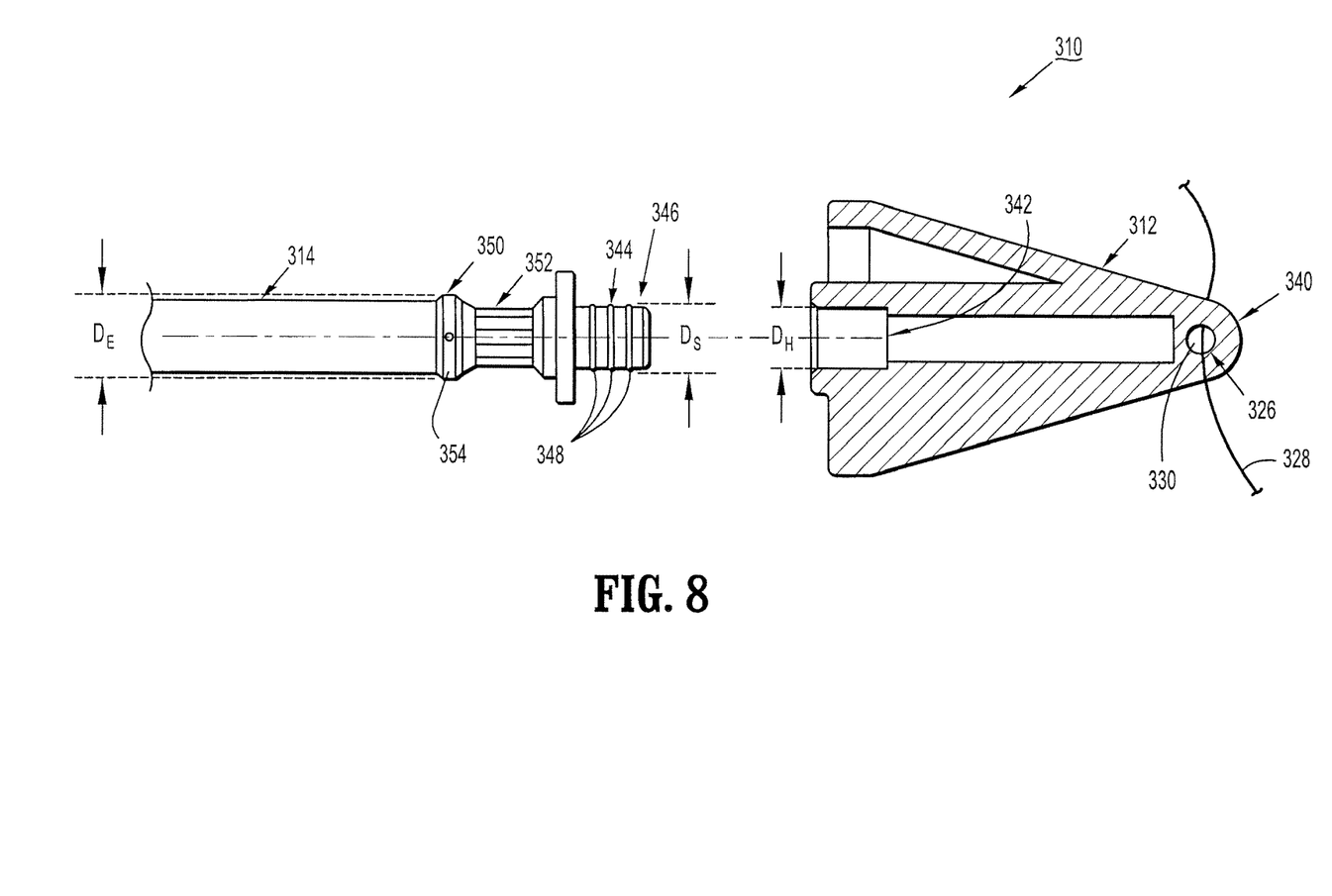
FIG. 8 is a side view of an alternate embodiment of the insertion device of FIG. 1 shown in a disassembled condition with the head separated from the shaft.
Figure 9:
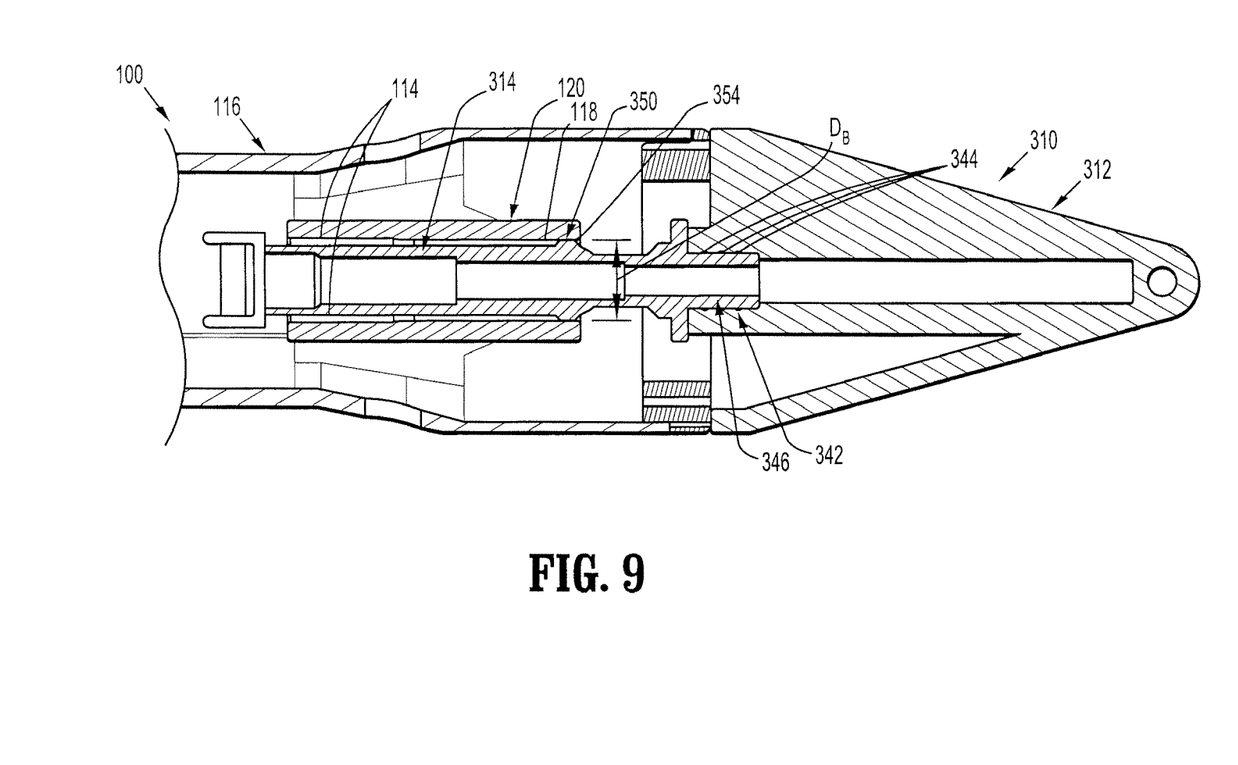
FIG. 9 is a cross-sectional view of the insertion device of FIG. 8 shown in an assembled condition and after attachment to the fastening apparatus seen in FIG. 2.

Referring now to FIGS. 2 and 8-9, an alternate embodiment of the insertion device, referred to generally by reference number 310, will be discussed in connection with the fastening apparatus 100. The insertion device 310 includes a head 312 and a shaft 314, and is similar to the insertion device 10 discussed above with respect to FIGS. 1-7. Accordingly, the insertion device 310 will only be discussed with respect to its differences from the insertion device 10.

The head 312 defines a generally conical configuration having a substantially blunt distal end 340 to facilitate atraumatic insertion. The distal end 340 includes the aforedescribed attachment surface 326 for the reception of a removal member 328. While the embodiment of the head 312 seen in FIGS. 8-9 depicts the attachment structure 326 as including a throughbore 330 that extends through the head 312, alternate configurations for the attachment structure 326 are also within the scope of the present disclosure. The head 312 further includes internal receipt structure 342 to facilitate attachment of the head 312 to the shaft 314, and thus, assembly of the insertion device 310.

The shaft 314 extends proximally from the head 312 and includes attachment structure 344 formed at the distal end 346 thereof that is configured and dimensioned to frictionally engage, and mechanically cooperate with, the receipt structure 342 formed in the head 312. In the particular embodiment seen in FIGS. 8-9, the attachment structure 344 includes a plurality of first ribs 348 extending radially outward from the distal end 346 of the shaft 314 such that the distal end 346 defines a transverse dimension "$D_S$". The transverse dimension "$D_S$" is greater than the internal transverse dimension "$D_H$" defined by the receipt structure 342 formed in the head 312 such that an interference fit is created upon insertion of the distal end 346 of the shaft 314 into the head 312, as seen in FIG. 9. It is contemplated that the head 312 and shaft 314 can be permanently affixed or removed attached by the aforedescribed structure or other structure.

The shaft 314 further includes an engagement member 350 located proximally of the plurality of splines 352 formed about the shaft 314, which mate with a plurality of corresponding grooves 114 formed in the shell assembly 116 of the fastening apparatus 100. In the particular embodiment seen in FIGS. 8-9, the engagement member 350 includes a second rib 354 extending outwardly from the shaft 314 to define a transverse dimension "$D_E$". The transverse dimension "$D_E$" is greater than an internal transverse dimension "$D_B$" defined by the internal wall 118 of the shell boss 120 component of the shell assembly 116. The engagement member 350 frictionally engages, and mechanically cooperates with, the internal wall 118 to create an interference fit which ensures that the insertion device 310 remains attached to the fastening apparatus 100 during insertion, e.g., by preventing inadvertent displacement of the insertion apparatus 310. When disconnection of the insertion device 310 from the fastening apparatus 100 is desired, the clinician manipulates the approximation knob 122 (FIG. 2) of the handle assembly 102 to advance the retaining member 108 (FIG. 2), and thus, the insertion device 310, distally. As the insertion device 310 is advanced distally, the engagement member 350 is forced out of contact with the internal wall 118 of the shell boss 120, thereby facilitating removal of the insertion device 310 from the fastening apparatus 100. Further details regarding the components and structure of the fastening apparatus 100 can be obtained through reference to U.S. Pat. No. 7,303,106, the entire contents of which are incorporated by reference herein.

In one embodiment, the apparatus 100 is packaged with the insertion device connected to the retaining member 108 and the instrument approximately ¾ clamped (about one full turn from full approximation). In this packaged configuration, the apparatus is ready for insertion, with the insertion device secured on the instrument, but the safety cannot be disengaged so the surgeon cannot inadvertently fire the instrument (unless the surgeon further approximates the instrument). For removal of the insertion device, the instrument can be unclamped (unapproximated) in the manner described above.

While the attachment structure 344 and the engagement member 350 included on the shaft 314 are respectively illustrated as first and second ribs 348, 354, in alternate embodiments, the attachment structure 344 and the engagement member 350 may be configured as any protrusion suitable for the intended purpose of creating an interference fit with the head 312 and the fastening apparatus 100, respectively, including but not being limited to spherical bumps or the like. In one embodiment, four ribs or four bumps are provided, although a different number is also contemplated to achieve the attachment function.

The insertion devices disclosed herein can be reusable (re-sterilized) and made of material such as aluminum, or can be disposable (single use) made of material such as plastic. In one embodiment of the metal version, the shaft and head are welded together. In one embodiment of the plastic version, the shaft and head are ultrasonically welded together. In a preferred embodiment of the reusable insertion device, four ribs for providing an interference fit with the instrument retainer are provided. In a preferred embodiment of the reusable version, four substantially spherical bumps are provided.

It will be understood that various modifications can be made to the embodiments disclosed herein. For example, as noted hereinabove, the disclosed embodiments are suitable for use with various surgical fastening apparatus and can be varied to accommodate the same. Additionally, the various embodiments need not prevent activation of the tissue fastening apparatus but can be dimensioned and configured to provide ease of insertion only. Therefore, the above description should not be construed as limiting, but merely as exemplifications of preferred embodiment. Those skilled in the art will envision other modifications within the scope and spirit of the claims appended hereto.

What is claimed is:

1. An insertion device configured for releasable engagement with a surgical fastening apparatus having a retaining member for releasably engaging an anvil assembly, the insertion device comprising:
    a shaft having a proximal end including an engagement member configured to frictionally engage a distal end of the surgical fastening apparatus such that an interference fit is created therebetween, the interference fit configured to facilitate selective detachment of the insertion device from the surgical fastening apparatus to enable subsequent attachment of an anvil assembly to the surgical fastening apparatus, wherein the shaft is configured to be detachable from the surgical fastening apparatus in response to advancement of the retaining member of the surgical fastening apparatus from the distal end of the surgical fastener apparatus; and
    a head supported on a distal end of the shaft, the head having a distal end defining an atraumatic configuration and being dimensioned to be received in a body orifice.

2. The insertion device of claim 1, further including at least one attachment surface, wherein the at least one attachment surface is configured as a throughbore formed in the head.

3. The insertion device of claim 2, wherein the at least one attachment surface is spaced distally from the distal end of the shaft.

4. The insertion device of claim 2, wherein the head has a reduced transverse dimension region, and the at least one attachment surface is on the reduced transverse dimension region.

5. The insertion device of claim 1, further including at least one attachment surface, wherein the at least one attachment surface includes a cross-member positioned within a recess defined in an external surface of the head.

6. The insertion device of claim 1, wherein a radius of the head is at least substantially equal to a radius of a distal end of the surgical fastening apparatus.

7. The insertion device of claim 1, wherein the head is formed integrally with the shaft.

8. The insertion device of claim 1, further including at least one attachment surface formed on the head configured to engage at least one removal member.

9. The insertion device of claim 8, wherein the at least one removal member includes a first end and a second end, at least the first end being in engagement with the at least one attachment surface.

10. The insertion device of claim 8, wherein the at least one removal member is selected from the group consisting of a suture, a wire and a cable.

11. The insertion device of claim 1, wherein the shaft and the head include corresponding structure configured and dimensioned to facilitate selective attachment of the shaft and the head.

12. The insertion device of claim 1, wherein the head supported on the distal end of the shaft includes a proximal end defining a continuous and planar surface.

13. An insertion device configured for releasable engagement with a surgical fastening apparatus having a retaining member for releasably engaging an anvil assembly, the insertion device comprising:
a shaft having a distal end and a proximal end, the proximal end including an engagement member configured to frictionally engage a distal end of the surgical fastening apparatus such that an interference fit is created therebetween, the interference fit configured to facilitate selective detachment of the insertion device from the surgical fastening apparatus to enable subsequent attachment of an anvil assembly to the surgical fastening apparatus, wherein the shaft is configured to be detachable from the surgical fastening apparatus in response to advancement of the retaining member of the surgical fastening apparatus from the distal end of the surgical fastener apparatus, the shaft including at least one protrusion extending radially outward from the distal end of the shaft to define a first transverse dimension; and
a head supported on a distal end of the shaft, the head having a distal end defining an atraumatic configuration and being dimensioned to be received in a body orifice, the head including an internal receipt structure defining a second transverse dimension,
wherein the first transverse dimension of the shaft is greater than the second transverse dimension of the head such that the shaft frictionally engages the head to establish an interference fit therebetween upon assembly.

14. The insertion device of claim 13, wherein the at least one protrusion is configured as a rib.

15. The insertion device of claim 1, wherein the engagement member is configured and dimensioned to frictionally engage an internal wall at the distal end of the surgical fastening apparatus.

16. The insertion device of claim 15, wherein the engagement member includes at least one protrusion extending radially outward from the shaft to define a first transverse dimension, and the internal wall at the distal end of the surgical fastening apparatus defines a second transverse dimension, the first transverse dimension being greater than the second transverse dimension to create an interference fit between the engagement member and the internal wall.

17. The insertion device of claim 16, wherein the at least one protrusion is configured as a rib.

18. A surgical fastening apparatus comprising:
an elongated body portion;
a head portion supported on the elongated body portion and including a retaining member, the retaining member being movable between a retracted position and an advanced position; and
an insertion device configured to releasably engage the retaining member, the insertion device including:
a shaft including a proximal end having an engagement member configured to frictionally engage the retaining member of the surgical fastening apparatus such that an interference fit is created therebetween, the interference fit configured to facilitate selective detachment of the insertion device from the surgical fastening apparatus to enable subsequent attachment of an anvil assembly to the surgical fastening apparatus, wherein the shaft is configured to be detachable from the retaining member in response to advancement of the retaining member from the retracted position toward the advanced position; and
a head supported on a distal end of the shaft, the head having a distal end defining an atraumatic configuration and being dimensioned to be received in a body orifice.

19. The surgical fastening apparatus of claim 18, wherein the insertion device further includes at least one attachment surface, wherein the at least one attachment surface is configured as a throughbore formed in the head of the insertion device.

20. The surgical fastening apparatus of claim 18, wherein the insertion device further includes at least one attachment surface, wherein the at least one attachment surface includes a cross-member positioned within a recess defined in an external surface of the head.

21. The surgical fastening apparatus of claim 18, wherein a radius of the head of the insertion device is at least substantially equal to a radius of the head portion.

22. The surgical fastening apparatus of claim 18, wherein the head of the insertion device is formed integrally with the shaft of the insertion device.

* * * * *